United States Patent [19]

Wilk et al.

[11] Patent Number: 5,396,879
[45] Date of Patent: Mar. 14, 1995

[54] ELONGATE MEDICAL INSTRUMENT WITH DISTAL END ORIENTATION CONTROL

[76] Inventors: Peter J. Wilk, 185 W. End Ave., New York, N.Y. 10023; Naomi L. Nakao, 303 E. 57th St., New York, N.Y. 10022

[21] Appl. No.: 866,815

[22] Filed: Apr. 9, 1992

[51] Int. Cl.⁶ .................... A61B 1/04; A61M 25/01
[52] U.S. Cl. ............................. 128/4; 604/95; 604/280
[58] Field of Search ............... 128/4, 6, 7–10, 128/657, 737, 772, 899, 748; 604/95, 156, 198; 227/178, 179; 901/2, 21, 39; 414/2, 4; 165/11.2; 175/261, 45

[56] References Cited

U.S. PATENT DOCUMENTS 4,758,222  7/1988  McCoy .

Primary Examiner—Richard J. Apley
Assistant Examiner—John P. Leubecker
Attorney, Agent, or Firm—R. Neil Sudol; Henry D. Coleman

[57] ABSTRACT

A medical device comprises an elongate insertion member such as a catheter or a laparoscopic instrument shaft having a flexible distal end portion, the insertion member being adapted for insertion into a patient, and a drive mounted to the insertion member about a distal end thereof for flexing the distal end portion of the insertion member. A power supply is operatively connected to the drive for energizing the drive, while a control component such as a wireless receiver is operatively connected to the drive for selectively controlling the energization thereof, thereby controlling the direction of flexing of the distal end portion. The receiver and the power supply are mounted to the insertion member proximally of the flexible distal end portion thereof.

12 Claims, 1 Drawing Sheet

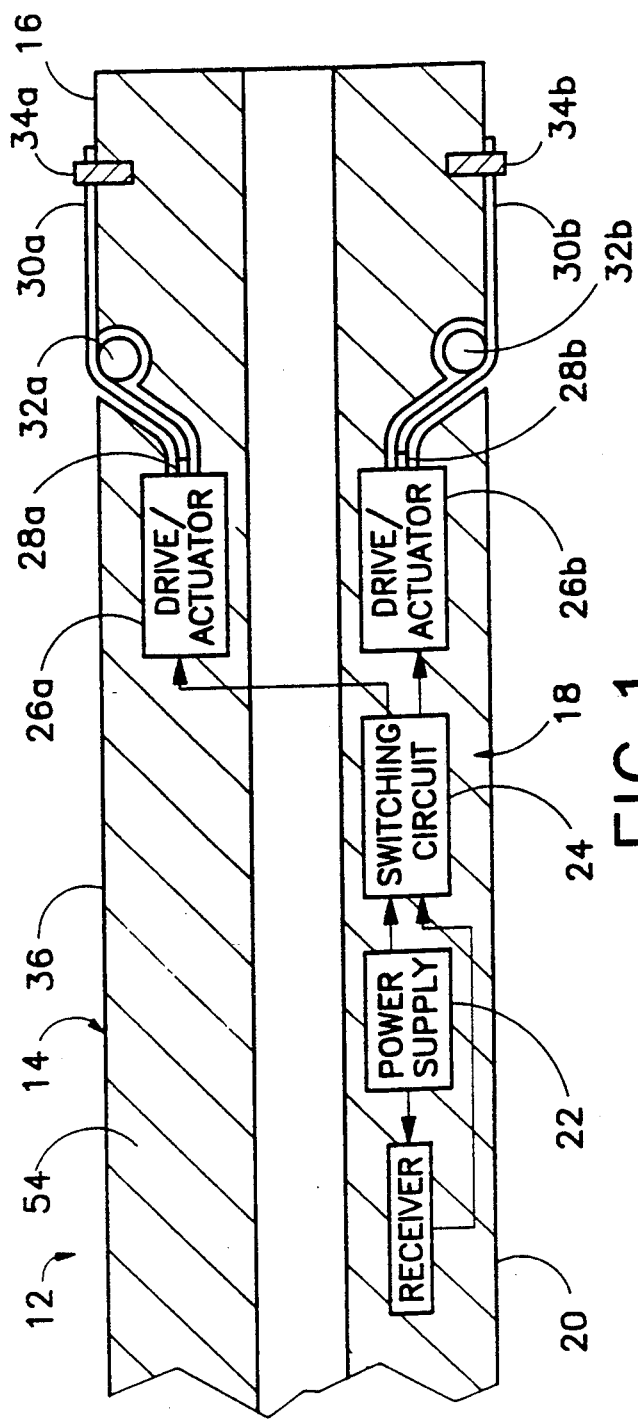
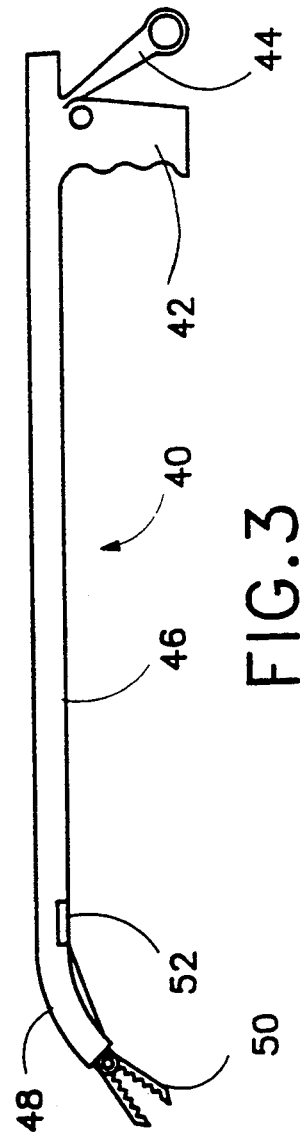
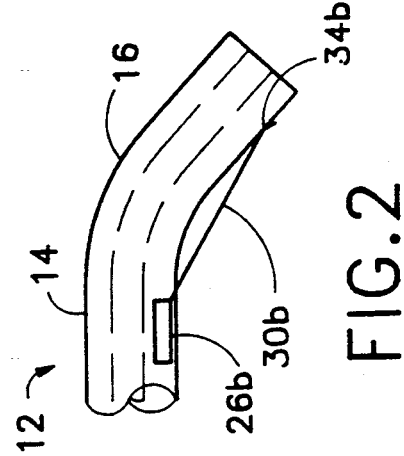

ELONGATE MEDICAL INSTRUMENT WITH DISTAL END ORIENTATION CONTROL

BACKGROUND OF THE INVENTION

This invention relates to an elongate, at least partially flexible instrument for insertion into a patient's body during a medical procedure. More particularly, the present invention relates to a device and method wherein the orientation of a distal end portion of such an elongate insertion member is controllable.

Typically, flexible endoscopic and laparoscopic insertion members have distal end portions whose orientations are controllable via a plurality of cables extending longitudinally along the insertion members from proximal ends thereof. Such a method for controlling orientation, however, is not utilizable with angiographic catheters. Such catheters are much thinner and usually longer than endoscopic or laparoscopic insertion members. Consequently, control of the distal end orientation of angiographic catheters is practically impossible via conventional cable mechanisms.

OBJECTS OF THE INVENTION

An object of the present invention is to provide a device or assembly for controlling distal end orientation of elongate medical instruments which are inserted into patients' bodies.

Another, more particular, object of the present invention is to provide such a device or assembly which is particularly practicable with angiographic catheters.

A further object of the present invention is to provide a new method for controlling the orientation of a flexible distal end portion of an elongate medical instrument when the instrument, or a distal segment thereof, is inserted into a patient.

Another particular object of the present invention is to provide such a method which is useful in angiographic applications.

SUMMARY OF THE INVENTION

A medical device comprises, in accordance with the present invention, an elongate insertion member having a flexible distal end portion, the insertion member being adapted for insertion into a patient, and an energizable drive mounted to the insertion member about a distal end thereof for flexing the distal end portion of the insertion member. A power supply is operatively connected to the drive for energizing the drive, while a control component is operatively connected to the drive for selectively controlling the energization thereof, thereby controlling the direction of flexing of the distal end portion.

Pursuant to another feature of the present invention, the drive includes a plurality of actuators mounted to the insertion member proximally of the distal end portion of the insertion member. The actuators have moving components connected to the distal end portion. The actuators may, for example, take the form of minute motors, in which case the moving components are connected the rotors. The actuators may alternatively take the form of tiny solenoids, in which case the moving components are coupled to the armatures thereof.

Preferably, the control component includes a wireless receiver mounted to the elongate insertion member about the distal end thereof. The receiver is operatively connected to the actuators, either directly, or indirectly. In a specific embodiment of the invention, one or more switches controllable by the receiver are connected between the power supply and the actuators.

Pursuant to another feature of the present invention, the power supply is also mounted to the insertion member about the distal end thereof.

An insertion member with distal end orientation control in accordance with the present invention is especially useful if in the form of an angiographic catheter. However, such a device may also be used in other applications, such as laparoscopy, for controlling orientation of instruments such as laparoscopes and laparoscopic forceps, graspers, scissors, irrigators, etc.

Preferably, the drive elements or actuators are mounted to the insertion member proximally of the distal end portion. The drive elements or actuators have moving components connected to the distal end portion for bending the distal end portion relative to the body of the insertion member.

A method for use in a diagnostic or surgical application comprises, in accordance with the present invention, the steps of (a) inserting into a patient an elongate insertion member having a flexible distal end portion, (b) emitting a wireless signal towards the patient so that the signal is transmitted through organic tissues of the patient to a distal end of the insertion member, (c) receiving the wireless signal via a receiver mounted to the insertion member about a distal end thereof, and (d) in response to the reception of the wireless signal, automatically energizing a drive element connected to the insertion member about the distal end thereof and thereby bending the distal end portion.

An elongate medical device or instrument with distal end orientation control in accordance with the present invention provides a capability not readily obtainable through by conventional techniques. Distal end orientation control in accordance with the present invention is particularly efficacious in angiographic applications.

BRIEF DESCRIPTION OF THE DRAWING

FIG. 1 is partially a schematic longitudinal cross-sectional view, on a greatly enlarged scale, and partially a block diagram of a catheter provided with a distal end orientation control assembly, in accordance with the present invention.

FIG. 2 is a partial side elevational view of the catheter of FIG. 1, showing the catheter operated to have a bent distal end portion.

FIG. 3 is a schematic side elevational view of a laparoscopic instrument provided with a distal end orientation control assembly, in accordance with the present invention, showing a distal end portion of the laparoscopic instrument turned to the side.

DETAILED DESCRIPTION

As illustrated in FIG. 1, an angiographic catheter 12 comprises an elongate tubular member 14 have a flexible distal end portion 16. Proximally of distal end portion 16, catheter 12 is provided with an orientation control assembly 18 including a wireless receiver 20, a power supply 22, a switching circuit 24, and a plurality of energizable drive members or actuators 26a and 26b all mounted inside or at least substantially embedded in the wall of a relatively long main body portion 54 of tubular member 14. Distal end portion 16 is movably connected to main body portion 54 for effectuating a steering of the catheter during use.

Receiver 10 is capable of receiving and demodulating wireless control signals arriving at distal end portion 16 through organic tissues of a patient into which catheter 12 has been inserted. A surgeon causes the generation of the wireless control signals by a transmitter (not illustrated) disposed outside the patient.

In response to the wireless control signals, receiver 20 induces switching circuit 24 to selectively connect actuators 26a and 26b to power supply 22. The actuator or actuators 26a or 26b so connected to power supply 22 are thereby energized to retract a respective plunger or rotor member 28a or 28b. Plungers 28a and 28b are connected to respective tension wires or threads 30a and 30b. The retraction of plunger 28a or 28b accordingly pulls a respective tension wire 30a or 30b and bends distal end portion 16 to the corresponding side, as shown in FIG. 2.

Wires 30a and 30b extend partially around guide elements or deflectors 32a and 32b and alongside an outer surface 36 of tubular member 14 to respective anchors 34a and 34b in distal end portion 16.

Actuators 26a and 26b preferably take the form of minute motors. However, other equivalent actuators are possible within the scope of the invention. Although only two actuators 26a and 26b are shown in FIG. 1, at least three and preferably four actuators are provided in order to fully control the orientation of distal end portion 16.

FIG. 3 illustrates a laparoscopic instrument 40 having a pair of handle actuators 42 and 44 connected to a proximal end of an elongate rigid shaft 46. Shaft 46 is provided with a flexible distal end portion 48 carrying an operative member 50 such as a forceps, graspers, scissors, etc. which is connected to handle actuators 42 and 44 for being operated thereby.

Laparoscopic instrument 40 is provided proximally of distal end portion 48 with the same distal end orientation control components as shown in FIG. 1, namely, a wireless receiver, a power supply, a switching circuit (none shown) and a plurality of motors or other drives 52.

Although the invention has been described in terms of particular embodiments and applications, one of ordinary skill in the art, in light of this teaching, can generate additional embodiments and modifications without departing from the spirit of or exceeding the scope of the claimed invention. For example, other drives equivalent to motors may be used, provided that sufficient displacement power is generated to bend the distal end portion of the catheter or, for example, a laparoscopic insertion member. Such equivalent bending drives may include solenoids or hydraulic mechanisms using a saline solution as a hydraulic fluid.

In addition, the wireless control of bending may find applications in areas of medicine other than laparoscopy and angiography. For example, certain endoscopic investigations or operations may benefit from wireless control. In addition, endotracheal tubes, Foley catheters, gastroesophageal tubes and other tubular inserts may have in some circumstances a distal end orientation control, as disclosed hereinabove with reference to FIG. 1, for facilitating placement of the respective flexible tube.

Accordingly, it is to be understood that the drawings and descriptions herein are proferred by way of example to facilitate comprehension of the invention and should not be construed to limit the scope thereof.

What is claimed is:

1. A medical device comprising:
an elongate catheter having a tubular body portion and a flexible distal end portion movably connected thereto to effect a steering of the catheter during use, said catheter being insertable into a patient, said catheter having a wall;
electromagnetic motor means substantially embedded in said wall of said catheter proximately to a junction between said tubular body portion and said distal end portion for flexing said distal end portion relative to said tubular body portion;
electrical power supply means operatively connected to said motor means for energizing same; and
control means operatively connected to said motor means for selectively controlling the energization thereof, thereby controlling the direction of flexing of said distal end portion wherein said control means includes a wireless receiver mounted to said catheter about a distal end thereof.

2. The device defined in claim 1 wherein said motor means includes a plurality of actuators each substantially embedded in said wall of said catheter proximally of said distal end portion, said actuators having moving components connected to said distal end portion.

3. The device defined in claim 2 wherein said power supply means is mounted to said catheter about the distal end thereof.

4. The device defined in claim 2 wherein said catheter is a catheter for use in angiography.

5. The device defined in claim 1 wherein said motor means is mounted to said catheter proximally of said distal end portion, said motor means including an actuator element connected to said distal end portion.

6. The device defined in claim 1 wherein said power supply means is mounted to said catheter about a distal end thereof.

7. An angiographic medical device comprising:
an elongate catheter having a tubular body portion and a flexible distal end portion movably connected thereto to effect a steering of the catheter during use, said catheter being adapted for insertion into a patient., said catheter having a wall;
at least one electrical drive member substantially embedded in said wall of said catheter proximately to a junction between said tubular body portion and said distal end portion for flexing said distal end portion relative to said tubular body portion;
at least one movable component operably connecting said drive member and said distal end portion;
electrical power supply means operatively connected to said drive member for energizing said drive member; and
wireless receiver means mounted to said catheter essentially at said distal end portion and operatively connected to said drive member for receiving wireless signals and selectively energizing said drive member to control the direction of flexing of said distal end portion in response to the received wireless signals.

8. The device defined in claim 7 wherein said power supply means and said receiver means are substantially embedded in said wall of said catheter.

9. The device defined in claim 7 wherein said wireless receiver means is substantially embedded in said wall of said catheter.

10. A method for use in a diagnostic or surgical application, comprising the steps of:

inserting into a patient an elongate catheter having a tubular body portion and a flexible distal end portion movably connected thereto to effect a steering of the catheter;

emitting a wireless signal towards the patient so that said signal is transmitted through organic tissues of the patient to a distal end of said catheter;

receiving said wireless signal via a receiver mounted to said catheter about a distal end thereof; and in response to the reception of said wireless signal, automatically energizing a drive element substantially embedded in a wall of said catheter about the distal end thereof to thereby bend said distal end portion relative to said tubular body portion.

11. The method defined in claim 10 wherein said step of inserting includes the step of inserting said catheter into a blood vessel of the patient.

12. The method defined in claim 10 wherein said drive element is a motor.

* * * * *